(12) United States Patent
Scribner et al.

(10) Patent No.: US 6,280,456 B1
(45) Date of Patent: Aug. 28, 2001

(54) METHODS FOR TREATING BONE

(75) Inventors: Robert M Scribner, Los Altos; Michael L Reo, Redwood City, both of CA (US)

(73) Assignee: Kyphon Inc, Sunnyvale, CA (US)

( * ) Notice: Subject to any disclaimer, the term of this patent is extended or adjusted under 35 U.S.C. 154(b) by 0 days.

(21) Appl. No.: 09/404,662

(22) Filed: Sep. 23, 1999

Related U.S. Application Data

(62) Division of application No. 08/911,827, filed on Aug. 15, 1997, now Pat. No. 5,972,015.

(51) Int. Cl.[7] .................................................. A61M 29/00
(52) U.S. Cl. ............................................. 606/192; 606/94
(58) Field of Search ................................... 606/192, 191, 606/193, 194, 195, 60, 61, 62, 94, 95; 604/96; 623/16, 17, 18, 19, 20, 21

(56) References Cited

U.S. PATENT DOCUMENTS

| | | |
|---|---|---|
| 5,090,957 | 2/1992 | Moutafis et al. . |
| 5,108,404 | 4/1992 | Scholten et al. . |
| 5,116,305 | 5/1992 | Milder et al. . |
| 5,176,692 | 1/1993 | Wilk et al. . |
| 5,263,931 | 11/1993 | Miller . |
| 5,275,622 | 1/1994 | Lazarus et al. . |
| 5,331,975 | 7/1994 | Bonnuti . |
| 5,749,888 | 5/1998 | Yock . |
| 5,766,151 | * 6/1998 | Valley et al. .............................. 604/96 |
| 5,788,703 | 8/1998 | Mittelmeier et al. . |
| 5,827,289 | * 10/1998 | Reiley et al. ............................ 606/86 |
| 6,132,824 | * 10/2000 | Hamlin .................................. 606/192 |

FOREIGN PATENT DOCUMENTS

| | | |
|---|---|---|
| WO 94/020166 | 9/1994 | (WO) . |
| WO 94/021320 | 9/1994 | (WO) . |

* cited by examiner

Primary Examiner—Henry J. Recla
Assistant Examiner—Lien Ngo
(74) Attorney, Agent, or Firm—Ryan Kromholz & Manion, S.C.

(57) ABSTRACT

A method for treating bone employs a tool comprising an outer catheter tube having a distal end and an inner catheter tube extending within the outer catheter tube and having a distal end region that extends beyond the distal end of the outer catheter tube. The tool includes an expandable structure having a proximal end secured to the distal end of the outer catheter tube and a distal end secured to the distal end region of the inner catheter tube. Thus, the distal end region of the inner catheter tube is enclosed within the expandable structure. The method manipulates the tool to introduce the expandable structure into bone while in a generally collapsed geometry. The method causes the expandable structure to assume an expanded geometry inside bone.

10 Claims, 13 Drawing Sheets

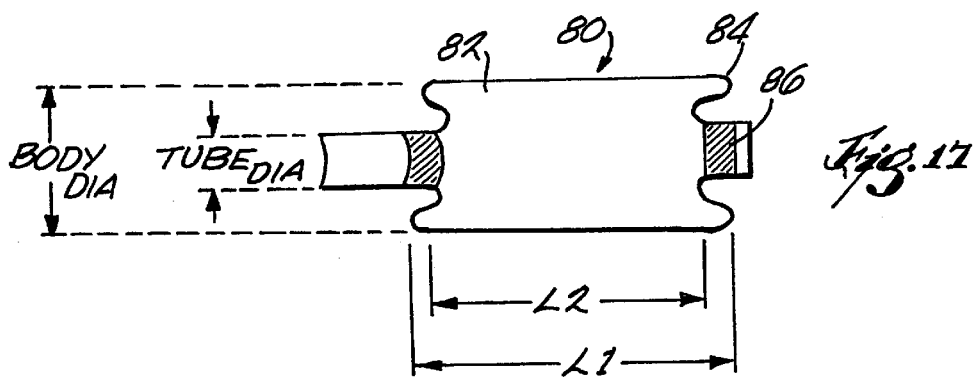
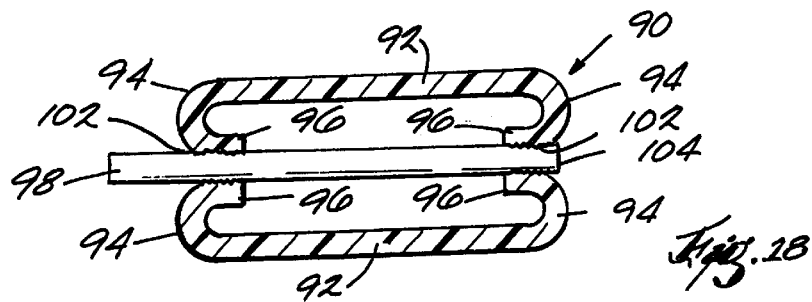
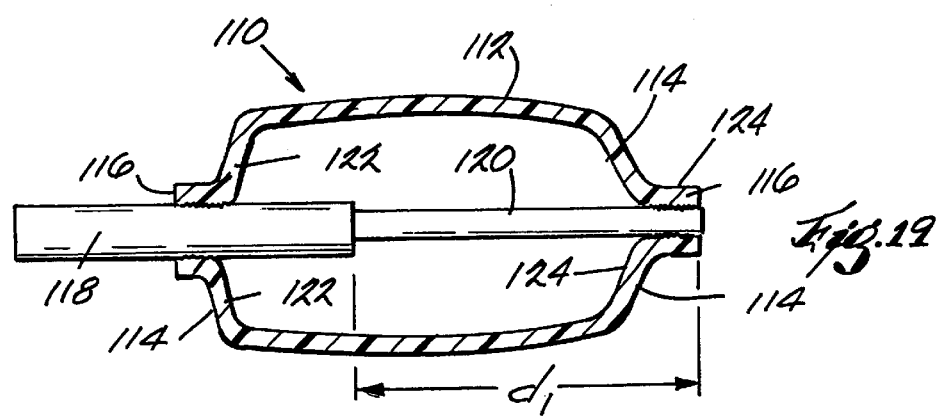
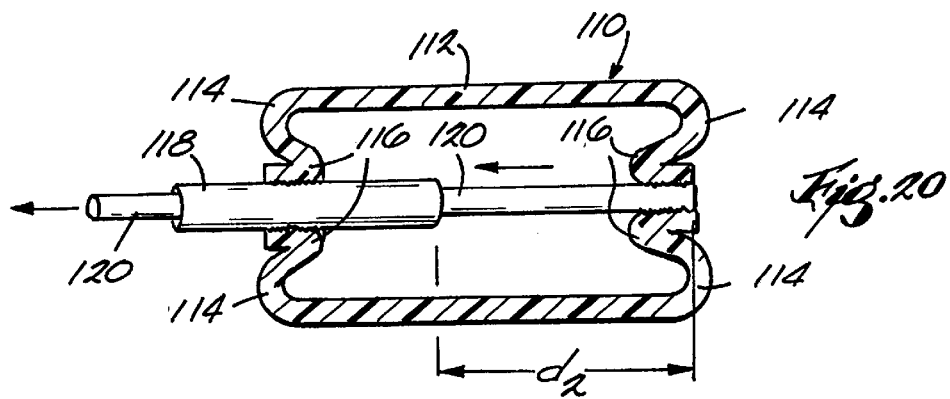

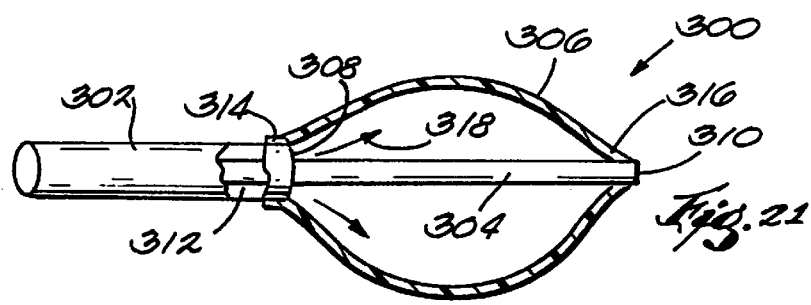
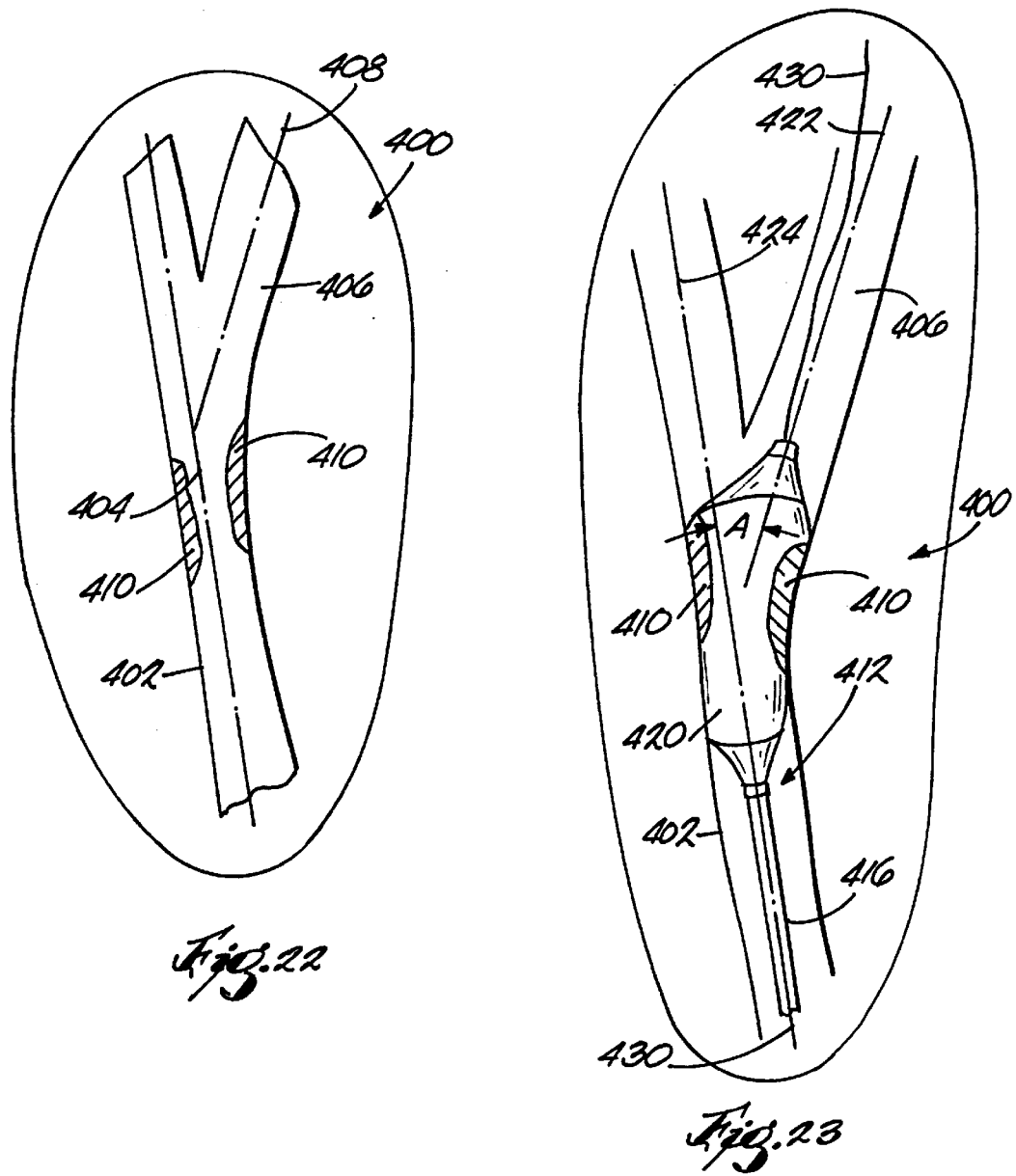

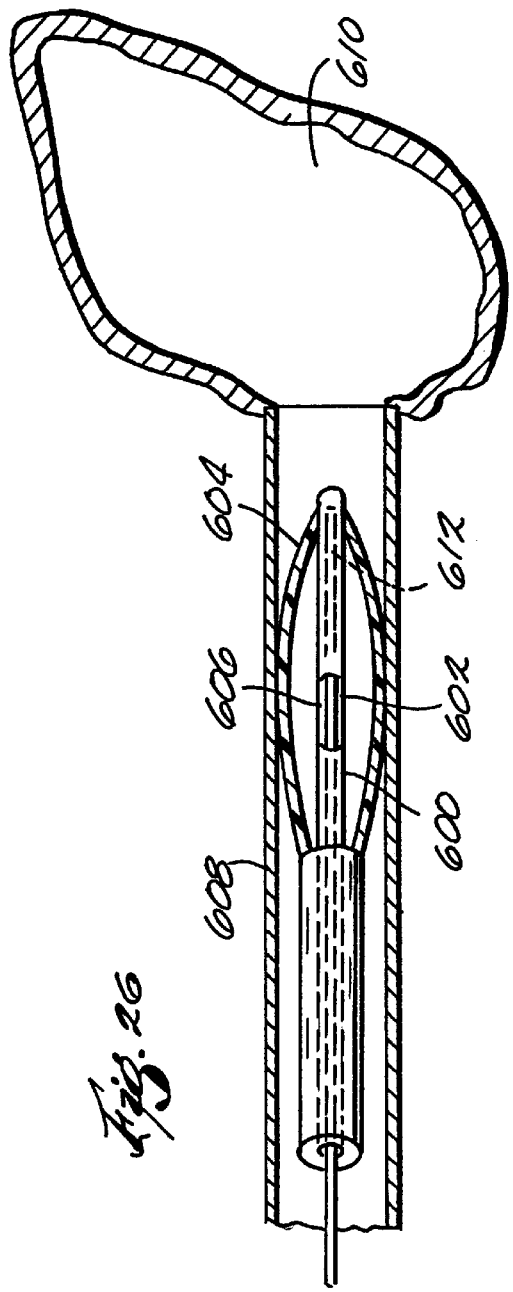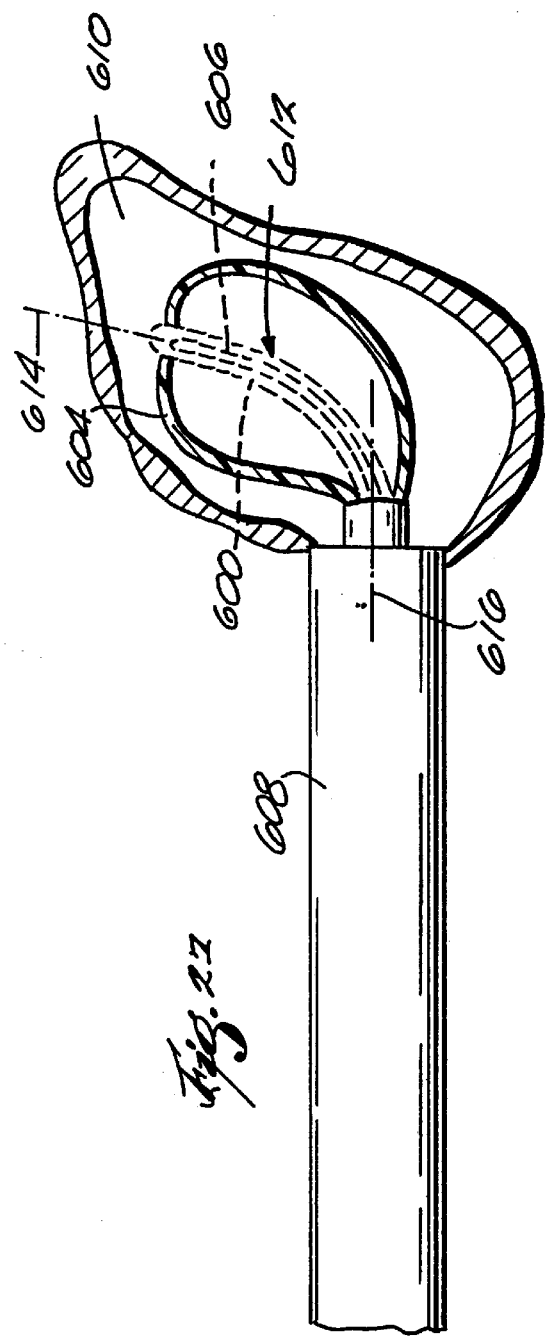

US 6,280,456 B1

METHODS FOR TREATING BONE

RELATED APPLICATION

This is a division of U.S. patent application Ser. No. 08/911,827 filed Aug. 15, 1997 now U.S. Pat. No. 5,972,015.

FIELD OF THE INVENTION

The invention relates to expandable structures, which, in use, are deployed in interior body regions of humans and other animals.

BACKGROUND OF THE INVENTION

The deployment of expandable structures into interior body regions is well known. For example, expandable structures, generically called "balloons," are deployed during angioplasty to open occluded blood vessels. As another example, U.S. Pat. Nos. 4,969,888 and 5,108,404 disclose apparatus and methods the use of expandable structures for the fixation of fractures or other osteoporotic and non-osteoporotic conditions of human and animal bones.

Many interior regions of the body, such as the vasculature and interior bone, possess complex, asymmetric geometries. Even if an interior body region is somewhat more symmetric, it may still be difficult to gain access along the natural axis of symmetry.

For example, deployment of an expandable structure in the region of branched arteries or veins can place the axis of an expandable structure off-alignment with the axis of the blood vessel which the structure is intended to occupy. As another example, insertion of an expandable structure into bone can require forming an access portal that is not aligned with the natural symmetry of the bone. In these instances, expansion of the structure is not symmetric with respect to the natural axis of the region targeted for treatment. As a result, expansion of the body is not symmetric with respect to the natural axis of the targeted region.

It can also be important to maximize the size and surface area of an expandable structure when deployed in an interior body region. Current medical balloons manufactured by molding techniques are designed to be guided into a narrow channel, such as a blood vessel or the fallopian tube, where they are then inflated. In this environment, the diameter of the balloon is critical to its success, but the length is less so. Such balloons only need to be long enough to cross the area of intended use, with few constraints past the effective portion of the inflated balloon. This allows conventional balloons to be constructed in three molded pieces, comprising a cylindrical middle section and two conical ends, bonded to a catheter shaft. As a practical matter, neither the length of the conical end, nor the length of the bond of the balloon to the catheter shaft, affect the function of conventional balloons, and these regions on conventional balloons are often 1 cm in length or more. Indeed, the larger the balloon diameter, the longer the end cone, which creates a tradeoff between maximum effective length and maximum effective diameter. This tradeoff makes optimization of conventional structures problematic in interior structures with defined lengths, such as bone.

SUMMARY OF THE INVENTION

The invention provides a method for treating bone. The method provides a tool comprising an outer catheter tube having a distal end and an inner catheter tube extending within the outer catheter tube and having a distal end region that extends beyond the distal end of the outer catheter tube. The tool includes an expandable structure having a proximal end secured to the distal end of the outer catheter tube and a distal end secured to the distal end region of the inner catheter tube. The distal end region of the inner catheter tube is enclosed within the expandable structure.

The method manipulates the tool to introduce the expandable structure into bone while in a generally collapsed geometry. The method causes the expandable structure to assume an expanded geometry inside bone.

In one embodiment, when assuming the expandable geometry, the expandable structure compacts cancellous bone. In one embodiment, the compaction forms a cavity. In one embodiment, the method conveys material, e.g., bone cement, into the cavity.

In one embodiment, when assuming the expandable geometry, the expandable structure exerts interior force upon cortical bone. In one embodiment, the interior force moves fractured cortical bone.

In one embodiment, the proximal and distal ends of the expandable structure are inverted about the distal end of the outer catheter tube and distal end region of the inner catheter tube, respectively.

In one embodiment, the inner catheter tube is more compliant than the outer catheter tube. In one embodiment, both the inner catheter tube and expandable structure are more compliant than the outer catheter tube.

Features and advantages of the inventions are set forth in the following Description and Drawings, as well as in the appended claims.

BRIEF DESCRIPTION OF THE DRAWINGS

FIG. 17 is a side view of an improved expandable structure, when in a substantially expanded condition, which includes end regions having compound curvatures that invert the end regions about the terminal regions, where the structure is bonded to the supporting catheter tube, to provide the capability of maximum bone compaction substantially along the entire length of the structure;

FIG. 18 is a side section view of an improved expandable structure, when in a substantially expanded condition, which includes end regions that have been tucked or folded about the terminal regions, where the structure is bonded to the supporting catheter tube, to provide the capability of maximum bone compaction substantially along the entire length of the structure;

FIG. 19 is a side section view of a tubular expandable structure having a distal end bonded to an inner catheter tube and a proximal end bonded to an outer catheter tube, the inner catheter tube being slidable within the outer catheter tube;

FIG. 20 is a side section view of the tubular expandable structure shown in FIG. 19, after sliding the inner catheter tube within the outer catheter tube to invert the end regions of the structure about the distal and proximal bonds, to thereby provide the capability of maximum bone compaction substantially along the entire length of the structure;

FIG. 21 is a side section view of a tubular expandable structure having a distal end bonded to an inner catheter tube and a proximal end bonded to an outer catheter tube, the inner catheter tube and structure being made of a more compliant material than the outer catheter tube to provide proportional length and diameter expansion characteristics;

FIG. 22 is an enlarged plan view of a branched blood vasculature region, in which an occlusion exists;

FIG. 23 is a further enlarged view of the branched blood vasculature region shown in FIG. 22, in which an asymmetric expandable structure of the type shown in FIG. 11 is deployed to open the occlusion;

FIG. 26 is a side view, with parts broken away and in section, of an expandable structure having an enclosed stiffening member, to straighten the structure during passage through a guide sheath into an interior body region; and FIG. 27 is a side view of the expandable structure shown in FIG. 27, after deployment beyond the guide sheath and into the interior body region, in which the stiffening member includes a distal region having a preformed bend, which deflects the structure relative to the axis of the guide sheath.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

The preferred embodiment first describes improved systems and methods that embody features of the invention in the context of treating bones. This is because the new systems and methods are advantageous when used for this purpose.

Another preferred embodiment describes the improved systems and methods in the context of relieving constrictions or blockages within branched blood vessels. This is because the vasculature also presents an environment well suited to receive the benefits of the invention.

The two environments are described for the purpose of illustration. However, it should be appreciated that the systems and methods as described are not limited to use in the treatment of bones or the vasculature. The systems and methods embodying the invention can be used virtually in any interior body region that presents an asymmetric geometry, or otherwise requires an access path that is not aligned with the natural axis of the region.

I. Deployment in Bones

The new systems and methods will be first described in the context of the treatment of human vertebra. Of course, other human or animal bone types, e.g., long bones, can be treated in the same or equivalent fashion.

Figure 1:
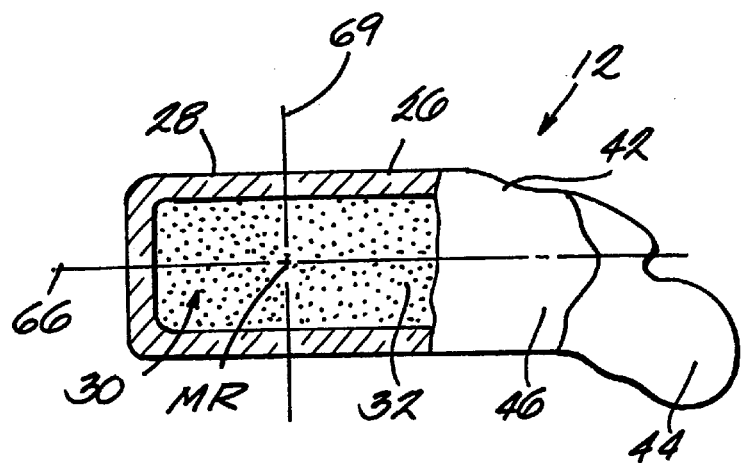
FIG. 1 is a lateral view, partially broken away and in section, of a lumbar vertebra taken generally along line 1—1 in FIG. 2.
Figure 2:
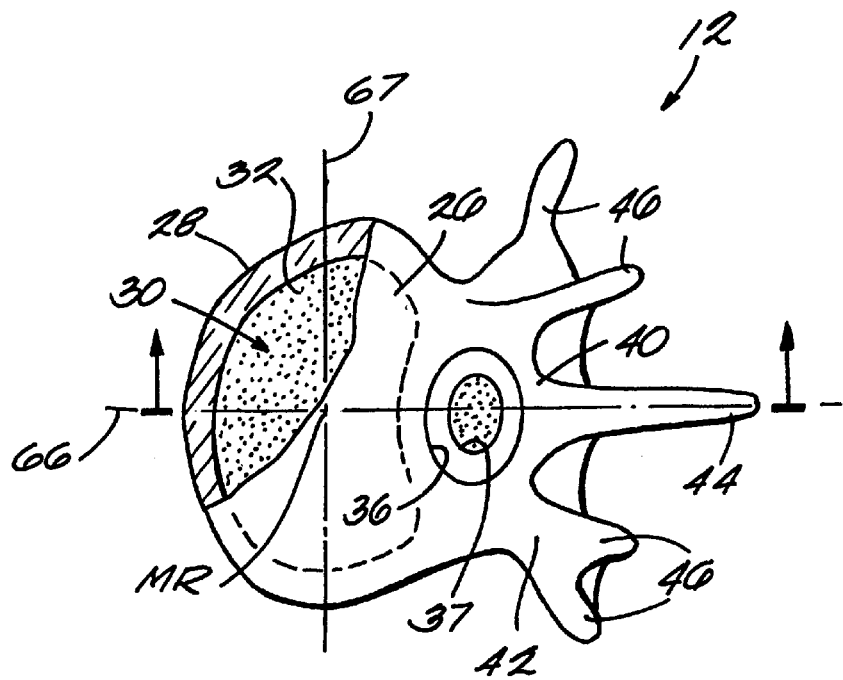
FIG. 2 is a coronal view of the lumbar vertebra, partially cut away and in section, shown in FIG. 1.

FIG. 1 shows a lateral (side) view of a human lumbar vertebra 12. FIG. 2 shows a coronal (top) view of the vertebra. The vertebra 12 includes a vertebral body 26, which extends on the anterior (i.e., front or chest) side of the vertebra 12. The vertebral body 26 is in the shape of an oval disk. The geometry of the vertebral body 26 is generally symmetric arranged about its natural mid-anterior-posterior axis 66, natural mid-lateral axis 67, and natural mid-top-to-bottom axis 69. The axes 66, 67, and 69 intersect in the middle region or geometric center of the body 26, which is designated MR in the drawings.

As FIGS. 1 and 2 show, the vertebral body 26 includes an exterior formed from compact cortical bone 28. The cortical bone 28 encloses an interior volume 30 of reticulated cancellous, or spongy, bone 32 (also called medullary bone or trabecular bone).

The spinal canal 36 (see FIG. 2), is located on the posterior (i.e., back) side of each vertebra 12. The spinal cord (not shown) passes through the spinal canal 36. The vertebral arch 40 surrounds the spinal canal 36. Left and right pedicles 42 of the vertebral arch 40 adjoin the vertebral body 26. The spinous process 44 extends from the posterior of the vertebral arch 40, as do the left and right transverse processes 46.

U.S. Pat. Nos. 4,969,888 and 5,108,404 disclose apparatus and methods for the fixation of fractures or other conditions of human and other animal bone systems, both osteoporotic and non-osteoporotic. The apparatus and methods employ an expandable structure to compress cancellous bone and provide an interior cavity. The cavity receives a filling material, e.g., bone cement, which hardens and provides renewed interior structural support for cortical bone. The compaction of cancellous bone also exerts interior force upon cortical bone, making it possible to elevate or push broken and compressed bone back to or near its original prefracture, or other desired, condition.

Figure 3:
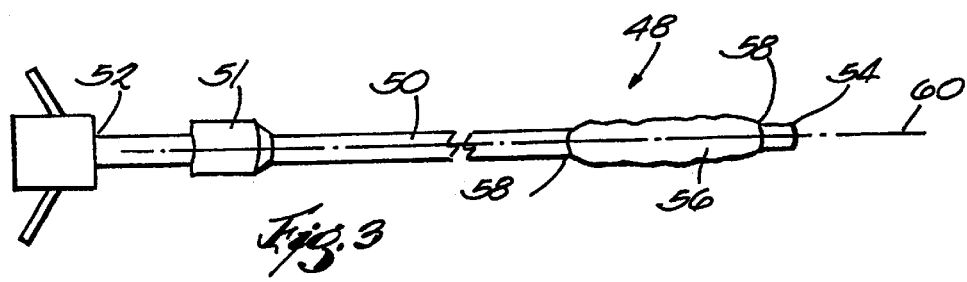
FIG. 3 is a top view of a probe including a catheter tube carrying a tubular expandable structure of conventional construction, shown in a substantially collapsed condition.

FIG. 3 shows a tool 48, which includes a catheter tube 50 having a proximal and a distal end, respectively 52 and 54. The catheter tube 50 includes a handle 51 to facilitate gripping and maneuvering the tube 50. The handle 51 is preferably made of a foam material secured about the catheter tube 50.

The distal end 54 carries an expandable structure 56, which FIG. 3 shows to be of conventional construction. The structure 56 is shown in FIG. 3 in a substantially collapsed geometry. The structure 56 conventionally comprises an elongated tube, formed, for example, by standard polymer extrusion and molding processes. The tubular structure 56 is bonded at its opposite ends 58 to the catheter tube 50, using, for example, an adhesive. When substantially collapsed, the structure 56 can be inserted into an interior body region.

Figure 4:
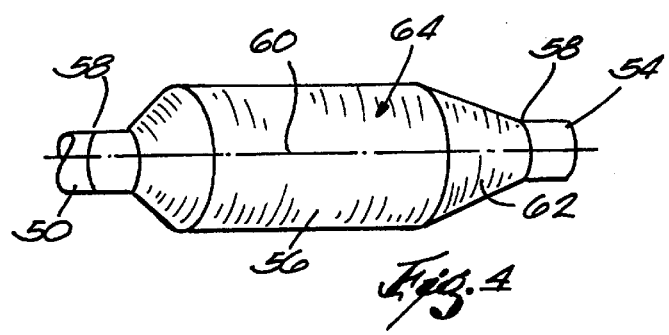
FIG. 4 is an enlarged side view of the tubular expandable structure carried by the probe shown in FIG. 3, shown in a substantially expanded condition.

Tubular bodies of the type shown in FIG. 3 are made from polymer materials and are commonly deployed in veins and arteries, e.g., in angioplasty applications. FIG. 4 shows an enlarged view of the structure 56 when in a substantially expanded geometry. As FIG. 4 shows, the middle region 64 of the tubular structure 56, when substantially expanded, assumes a generally cylindrical shape, which is symmetric about the main axis 60 of the catheter tube 50. Expansion stretches the polymer material of the structure 56 near its bonded ends 58 to form generally conical end portions 62.

Figure 5:
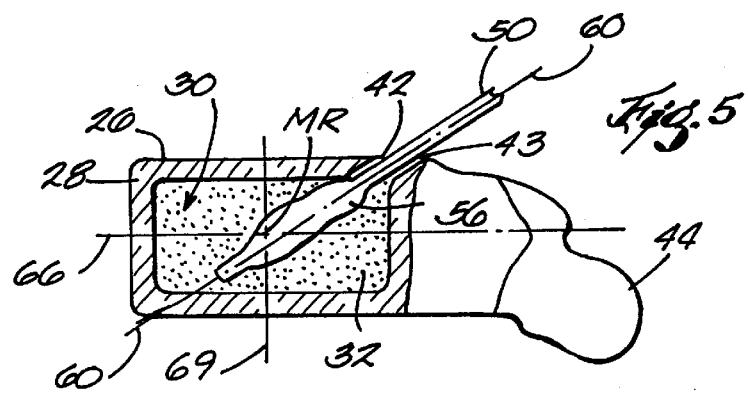
FIG. 5 is a lateral view of the lumbar vertebra shown in FIGS. 1 and 2, partially cut away and in section, with the expandable structure shown in FIGS. 3 and 4 deployed by transpedicular access when in a substantially collapsed condition.
Figure 6:
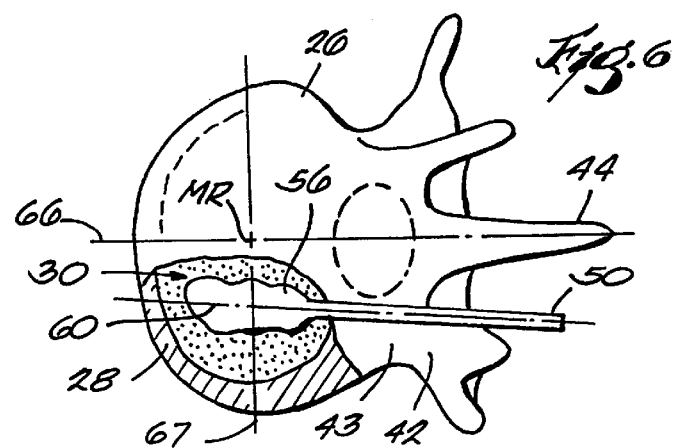
FIG. 6 is a coronal view of the transpedicular access shown in FIG. 5, partially cut away and in section.

The structure 56 can be inserted into bone in accordance with the teachings of the above described U.S. Pat. Nos. 4,969,888 and 5,108,404. For a vertebral body 26, access into the interior volume 30 can be accomplished, for example, by drilling an access portal 43 through either pedicle 42. This is called a transpedicular approach, which FIG. 5 shows in lateral view and FIG. 6 shows in coronal view. As FIG. 5 shows, the access portal 43 for a transpedicular approach enters at the top of the vertebral body 26, where the pedicle 42 is relatively thin, and extends at an angle downward toward the bottom of the vertebral body 26 to enter the interior volume 30. As FIGS. 5 and 6 show, in a typical transpedicular approach, the access portal 43 aligns the catheter tube axis 60 obliquely with respect to all natural axes 66, 67, or 69 of the vertebral body 26.

Figure 7:
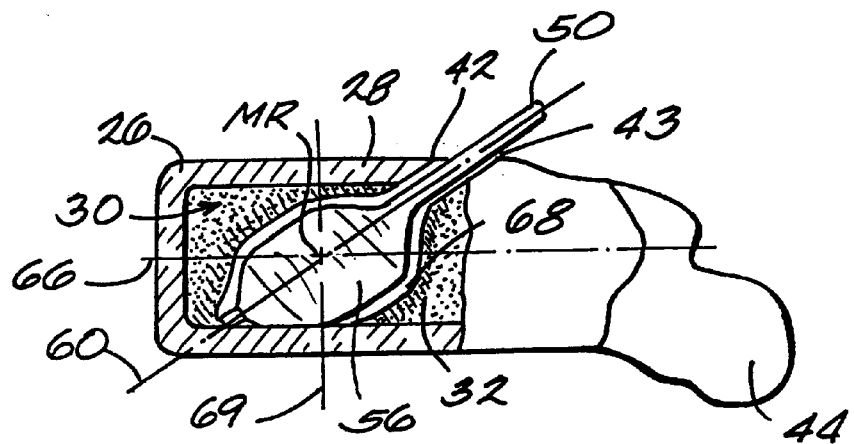
FIG. 7 is a lateral view of the transpedicular access shown in FIG. 5, with the expandable structure shown in FIGS. 3 and 4 in a substantially expanded condition, forming a cavity that is not centered with respect to the middle region of the vertebral body.
Figure 8:
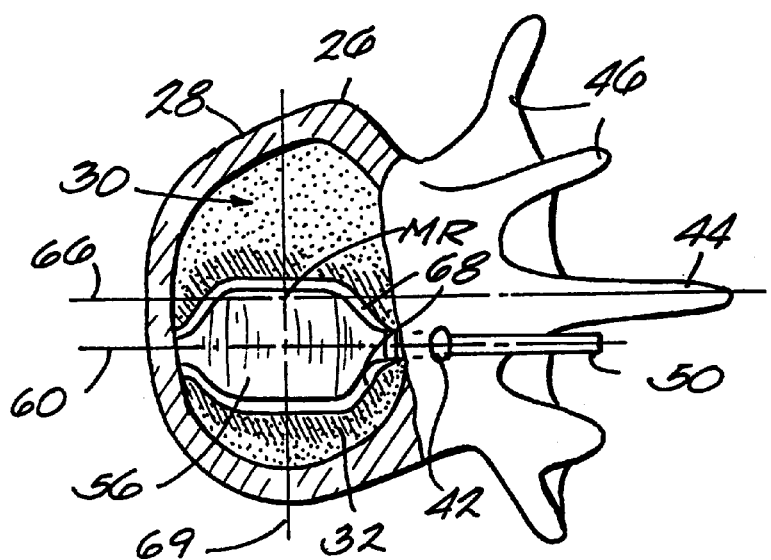
FIG. 8 is a coronal view of the transpedicular access shown in FIG. 7, partially cut away and in section.

As the conventional structure 56 expands within the interior volume 30 (as FIGS. 7 and 8 show, respectively, in lateral and coronal views for the transpedicular approach), the structure 56 symmetrically expands about the catheter tube axis 60, compressing cancellous bone 32 to form a cavity 68. However, since the catheter tube axis 60 is oriented obliquely relative to all natural axes 66, 67, or 69, the formed cavity is not centered with respect to the middle region MR. Instead, the cavity 68 is offset on one lateral side of the middle region MR (as FIG. 8 shows) and also extends from top to bottom at oblique angle through the middle region MR (as FIG. 7 shows).

Due to these asymmetries, the cavity 68 will not provide optimal support to the middle region MR when filled with bone cement. Since the bone cement volume is not centered about the middle region MR, the capability of the vertebral body 26 to withstand loads is diminished. The asymmetric compaction of cancellous bone 32 in the interior volume 30 may also exert unequal or nonuniform interior forces upon cortical bone 32, making it difficult to elevate or push broken and compressed bone.

Figure 9:
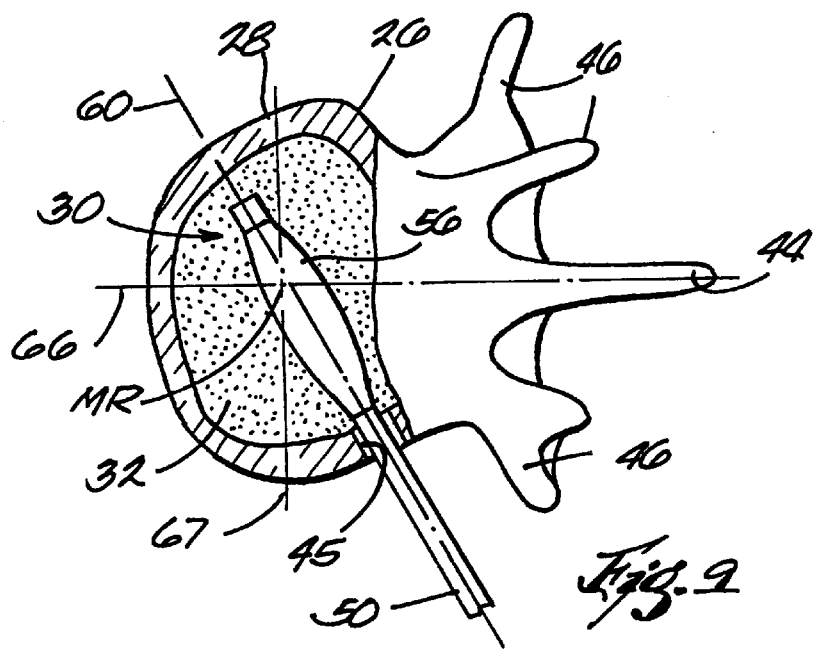
FIG. 9 is a coronal view of the lumbar vertebra shown in FIGS. 1 and 2, partially cut away and in section, with the expandable structure shown in FIGS. 3 and 4 deployed by postero-lateral access when in a substantially collapsed condition.

As FIG. 9 shows, access to the interior volume 30 of the vertebral body 26 also can be achieved by drilling an access portal 45 through a side of the vertebral body 26, which is called a postero-lateral approach. The portal 45 for the postero-lateral approach enters at a posterior side of the body 26 and extends at angle forwardly toward the anterior of the body 26.

Figure 10:
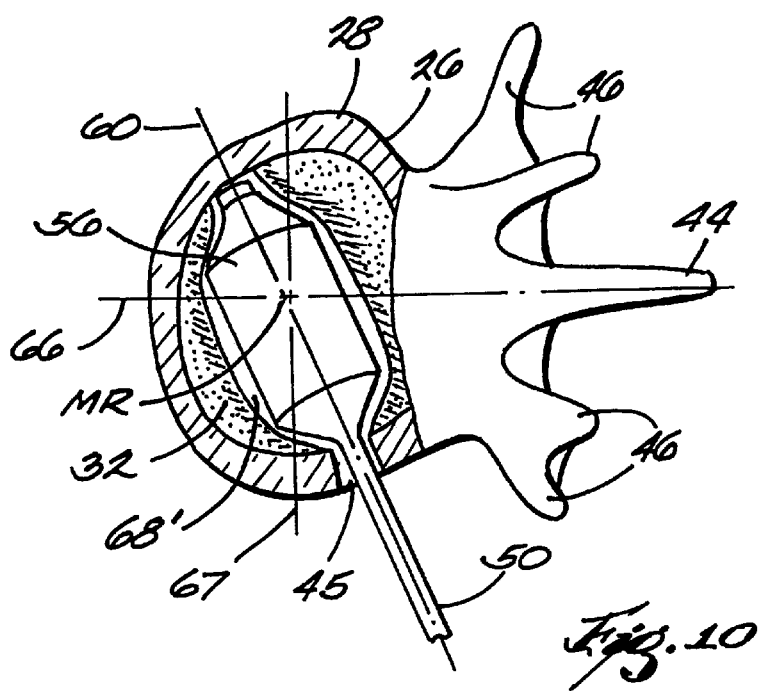
FIG. 10 is a coronal view of the postero-lateral access shown in FIG. 9, with the expandable structure shown in a substantially expanded condition, forming a cavity that is not centered with respect to the middle region of the vertebral body.

As FIG. 9 shows, the orientation of the portal 45 in a typical postero-lateral approach does not permit parallel or perpendicular alignment of the catheter tube axis 60 with either the mid-lateral axis 67 or the mid-anterior-posterior axis 66 of the vertebral body 26. As a result, symmetric expansion of the conventional structure 56 about the catheter tube axis 60 forms an off-centered cavity 68', which extends obliquely across the middle region MR of the body 26, as FIG. 10 view shows. As with the cavity 68 formed by the structure 56 using transpedicular access, the off-centered cavity 68' formed by the structure 56 using postero-lateral access also fails to provide optimal support to the middle region MR when filled with bone cement.

A. Optimal Orientation for Cancellous Bone Compaction

Figure 11A:
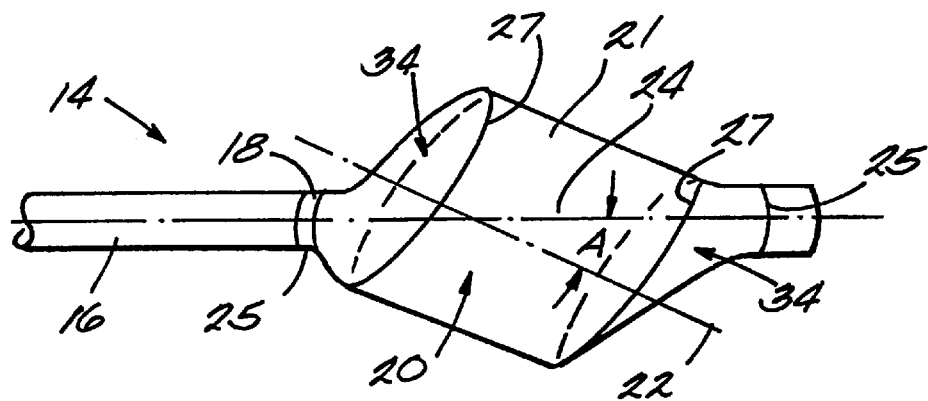
FIGS. 11A and 11B are side views of improved expandable structures, each having an axis of expansion that is offset by an acute angle and not aligned with the axis of the supporting catheter tube.

FIG. 11A shows an improved bone treating tool 14, which includes a catheter tube 16 carrying at its distal end 18 an expandable structure 20. The catheter tube 16 can, at its proximal end, be configured like the tube 50 shown in FIG. 3, with a handle 51 made of, e.g., a foam material.

FIG. 11A shows the structure 20 in a substantially expanded condition, in which the structure comprises a cylinder 21 with generally conical portions 34, each having a top 25 and a base 27. The tops 25 of conical portions 34 are secured about the catheter tube 16 and, in this respect, are generally aligned with the catheter tube axis 24. However, unlike the expandable structure 56 shown in FIG. 4, the main axis 22 of the cylinder 21 and the axis 24 of the catheter tube 16 are not aligned. Instead, the cylinder axis 22 is offset at an angle A from the catheter tube axis 24. As a result, the structure 20, when substantially expanded (as FIG. 11A shows), is not symmetric with respect to the catheter tube axis 24.

In FIG. 11A, the bases 27 of the conical portions 34 extend generally perpendicularly to the cylinder axis 22. In this orientation, the tops 25 and the bases 27 are not parallel to each other. Other orientations are possible. For example, in FIG. 11B, the bases 27 of the conical portions 34 extend generally perpendicularly to the catheter tube axis 24. In this orientation, the tops 25 and the bases 27 are generally parallel to each other.

Figure 12:
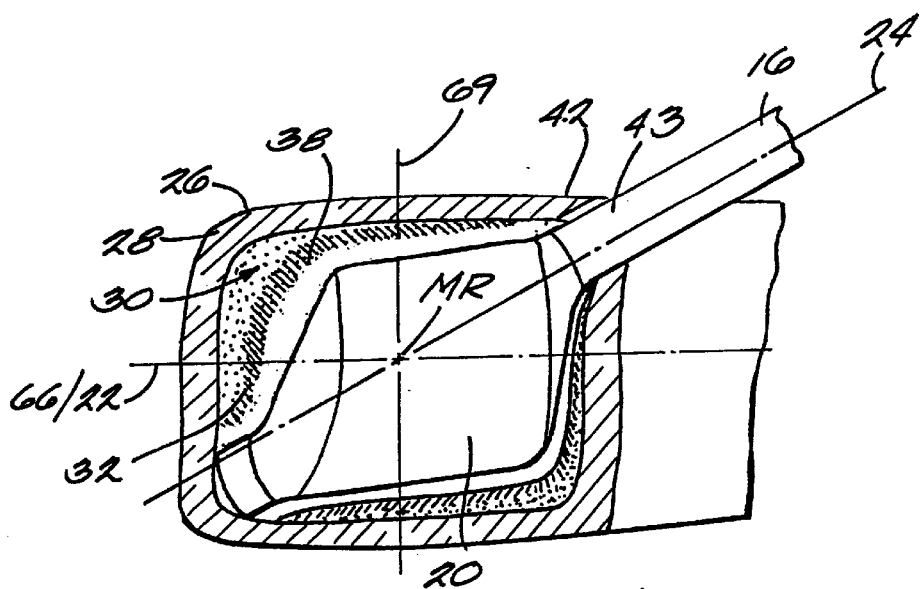
FIG. 12 is a lateral view of the lumbar vertebra shown in FIGS. 1 and 2, partially cut away and in section, with the offset expandable structure shown in FIG. 11A deployed by transpedicular access and being in a substantially expanded condition, forming a cavity that is substantially centered with respect to the middle region of the vertebral body.

FIG. 12 shows in lateral view, the offset structure 20 shown in FIG. 11A deployed by a transpedicular approach in the interior volume 30 of a vertebral body 26. As before shown in FIGS. 7 and 8, the transpedicular approach in FIG. 12 does not align the catheter tube axis 24 with any of the natural axes 66, 67, and 69 of the body 26. However, as FIG. 12 shows, the expansion of the offset cylinder 21 of the structure 20 about its axis 22 is not symmetric with respect to the catheter tube axis 24. Instead, expansion of the offset structure 20 is generally aligned with the natural axes 66 and 69 of the vertebral body 26.

As FIG. 12 shows, a single offset structure 20 introduced by transpedicular access, forms a cavity 38 that, while still laterally offset to one side of the middle region MR (as shown in FIG. 8), is nevertheless symmetric in a top-to-bottom respect with the middle region MR. A matching, adjacent cavity can be formed by transpedicular deployment of a second offset structure 20 on the opposite lateral side of the vertebral body 26. The composite cavity, formed by the two offset bodies 20, introduced simultaneously or in succession by dual transpedicular access, is substantially centered in all respects about the middle region MR.

Figure 13:
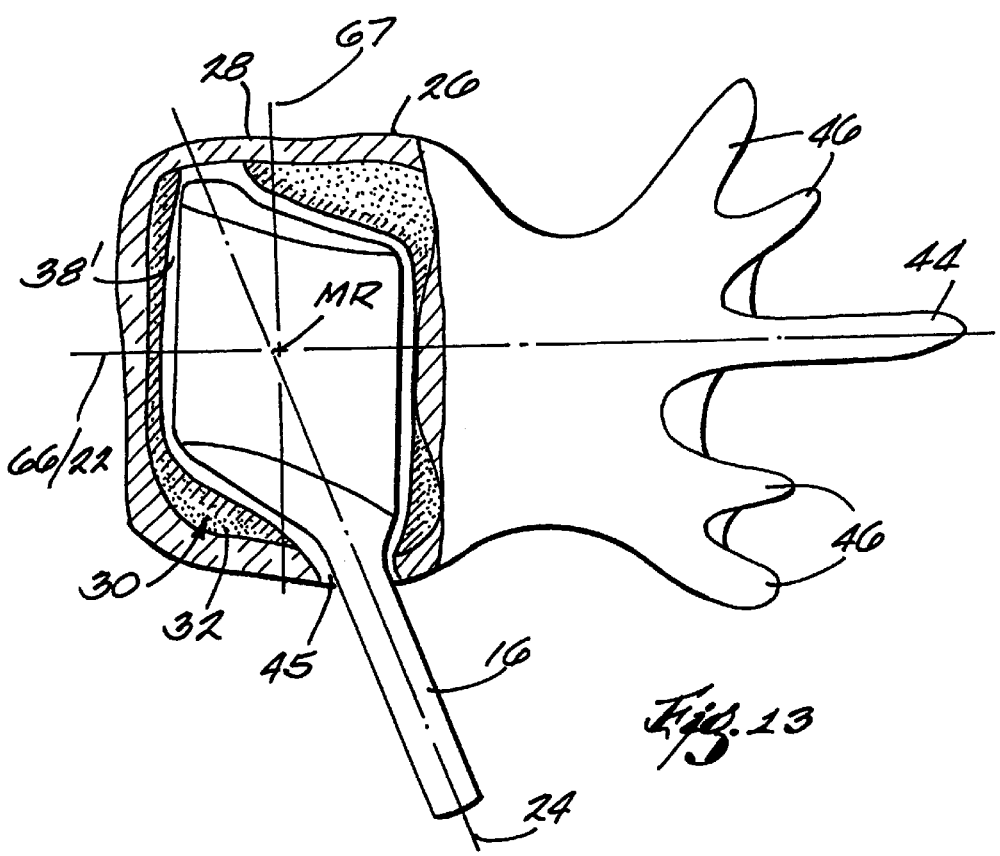
FIG. 13 is a coronal view of the lumbar vertebra shown in FIGS. 1 and 2, partially cut away and in section, with the offset expandable structure shown in FIG. 11 deployed by postero-lateral access and being in a substantially expanded condition, forming a cavity that is substantially centered with respect to the middle region of the vertebral body.

FIG. 13 shows the offset expandable structure 20 deployed by a postero-lateral approach in the interior volume 30 of a vertebral body 26. As before shown in FIG. 9, the postero-lateral approach in FIG. 13 does not align the catheter tube axis 24 with the natural axes 66 and 67 of the body 26. The expansion of the offset structure 20, which is asymmetric about the catheter tube axis 24, is nevertheless generally symmetric with respect to all natural axes 66, 67, and 69 of the vertebral body 26. A single offset structure 20, deployed by postero-lateral access, forms a cavity 38', which is substantially centered about the middle region MR.

A cavity centered with respect to the middle region MR provides support uniformly across the middle region MR when filled with bone cement. The capability of the vertebral body 26 to withstand loads is thereby enhanced. The symmetric compaction of cancellous bone 32 in the interior volume 30 that a centered cavity provides also exerts more equal and uniform interior forces upon cortical bone 32, to elevate or push broken and compressed bone.

Figure 11B:
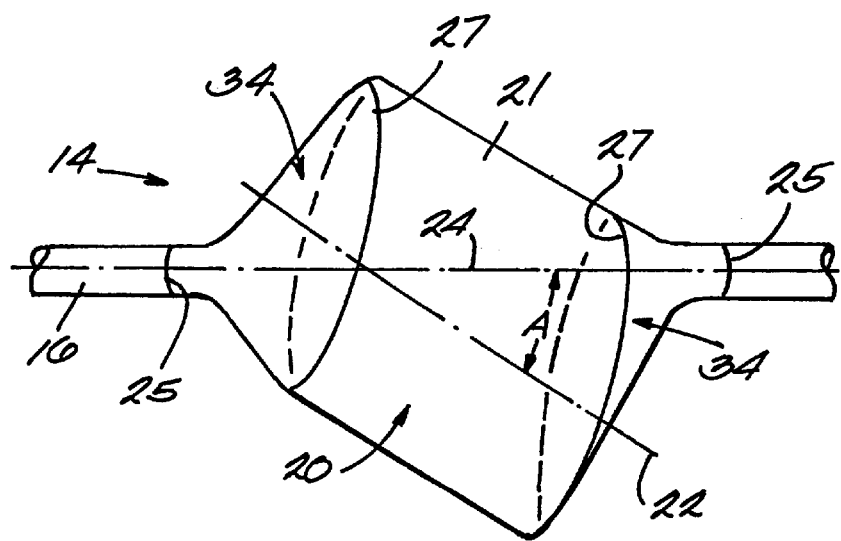
Figure 14A:
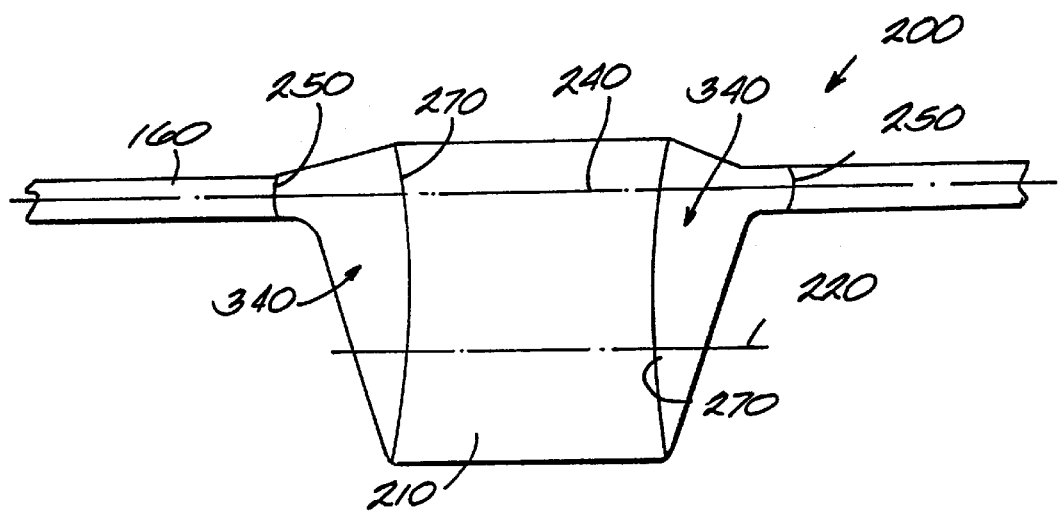
FIGS. 14A and 14B are side views of other embodiments of improved expandable structures, each having an axis of expansion that is offset by a distance from the axis of the supporting catheter tube.
Figure 14B:
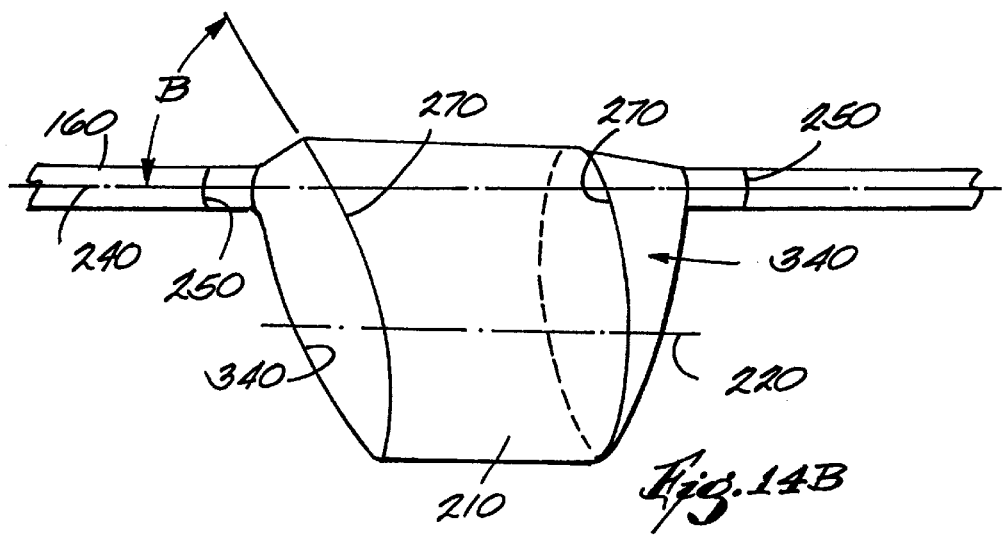

FIGS. 14A and 14B show an expandable structure 200 having an offset, asymmetric geometry different than the geometry of the offset expandable structure 20 shown in FIGS. 11A and 11B. In FIGS. 11A and 11B, the offset angle A between the cylinder axis 22 and the catheter tube axis 24 is an acute angle. As a result, the axis 22 of the structure 20 is offset in a nonparallel dimension or plane relative to the catheter tube axis 24. In FIGS. 14A and 14B, the offset angle A between the cylinder axis 220 and the catheter tube axis 240 is zero, as the axis 220 of the cylinder 210 is offset at a distance from and in a generally parallel dimension or plane relative to the catheter tube axis 240. The catheter tube 160 can, at its proximal end, be configured like the tube 50 shown in FIG. 3, with a handle 51 made of, e.g., a foam material.

As in FIGS. 11A and 11B, the tops 250 of conical portions 340 are secured about the catheter tube 160 and, in this respect, are generally aligned with the catheter tube axis 240. In FIGS. 14A and 14B, the orientation of the bases 270 of the conical portions 340 differ. In FIG. 14A, the bases 270 of the conical portions 340 extend generally perpendicularly to the catheter tube axis 240, and are, therefore generally parallel to the tops 250 (comparable to the orientation shown in FIG. 11B). In FIG. 14B, the bases 270 of the conical portions 340 extend at an angle B to the catheter tube axis 240. In this orientation, the tops 250 and the bases 270 are not parallel to each other.

FIGS. 11A and 11B and 14A and 14B show that it is possible, by adjustment of the offset angle A, as well as adjustment of the orientation of the conical end bases, to achieve virtually any desired offset geometry, and thereby tailor the orientation of the expandable structure to the particular geometry of the point of use.

B. Maximizing Cancellous Bone Compaction

Figure 15:
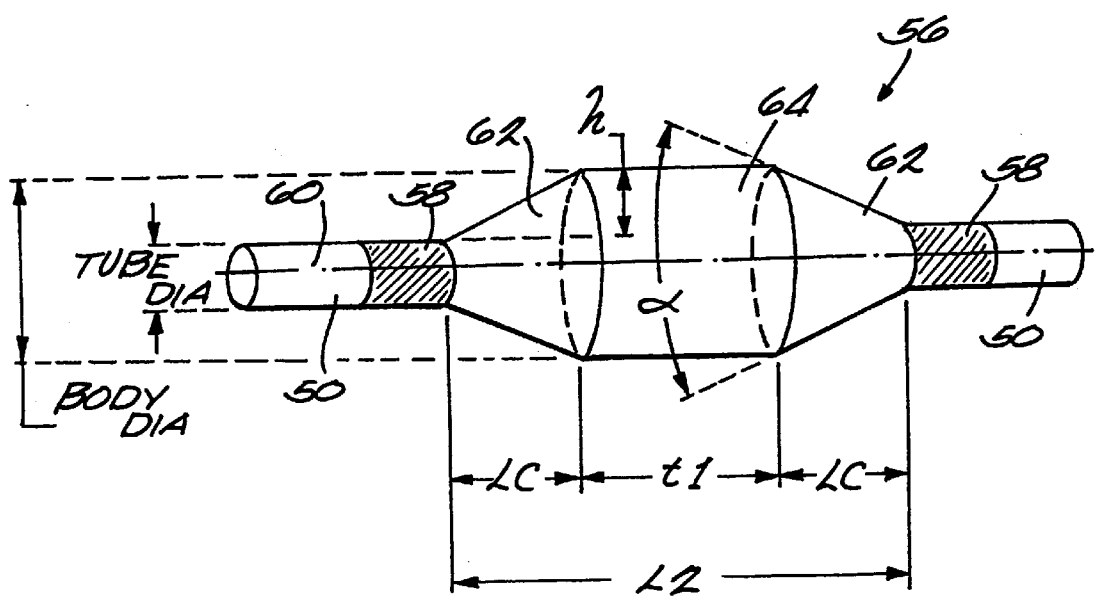
FIG. 15 is a side view of a conventional expandable structure shown in FIG. 4, enlarged to show further details of its geometry when substantially expanded.

Referring back to FIG. 4, when the conventional tubular structure 56 shown in FIG. 4 is substantially expanded, material of the structure is stretched into conical sections 62 near the ends 58, which are bonded to the catheter tube 50. FIG. 15 shows the geometry of expanded tubular structure 56 in greater detail. The conical portions 62 extend at a cone angle α from the bonded ends 58. The expanded structure 56 therefore presents the generally cylindrical middle region 64, where the maximum diameter of the structure 56. ($BODY_{DIA}$) exists, and the conical portions 62, which comprise regions of diameter that decreases with distance from the middle region 64 until reaching the diameter of the catheter tube ($TUBE_{DIA}$).

Due to the geometry shown in FIG. 15, maximum cancellous bone compaction does not occur along the entire length (L2) of the conventional structure 56, as measured between the bonded ends 58. Instead, maximum cancellous bone compaction occurs only along the effective length (L1) of the cylindrical middle region 64 of the structure 56, where the structure 56 presents its maximum diameter $BODY_{DIA}$. Cancellous bone compaction diminishes along the length of the conical portions 62, where the structure's diameter progressively diminishes. At the bonded ends 58, and portions of the catheter tube 50 extending beyond the bonded ends 58, no bone compaction occurs. The catheter tube 50 can, at its proximal end, be configured like the tube 50 shown in FIG. 3, with a handle 51 made of, e.g., a foam material.

The lengths (Lc) of the conical regions 62 and bonded ends 58 relative to the entire length of the structure 56 (L2) are important indications of the overall effectiveness of the structure 56 for compacting cancellous bone. The effective bone compaction length (L1) of any expandable structure having conical end regions, such as structure 56 shown in FIG. 15, can be expressed as follows:

$$L1 = L2 - 2(Lc)$$

where the length of a given conical region (Lc) can be expressed as follows:

$$Lc = \frac{h}{\tan\frac{\alpha}{2}}$$

where:

$$h = \frac{BODY_{DIA} - TUBE_{DIA}}{2}$$

where (see FIG. 15):

$BODY_{DIA}$ is the maximum diameter of the middle region 64, when substantially expanded, $TUBE_{DIA}$ is the diameter of the catheter tube 50, and α is the angle of the conical portion.

As the foregoing expressions demonstrate, for a given conical angle α, the length Lc of the conical portions 62 will increase with increasing maximum diameter $BODY_{DIA}$ of the middle region 64. Thus, as $BODY_{DIA}$ is increased, to maximize the diameter of the formed cavity, the lengths Lc of the conical portions 62 also increase, thereby reducing the effective length L1 of maximum cancellous bone compaction.

The bone compaction effectiveness of an expandable structure of a given maximum diameter increases as L1 and L2 become more equal. The geometry of a conventional tubular structure 56 shown in FIG. 15 poses a tradeoff between maximum compaction diameter and effective compaction length. This inherent tradeoff makes optimization of the structure 56 for bone compaction application difficult.

Figure 16:
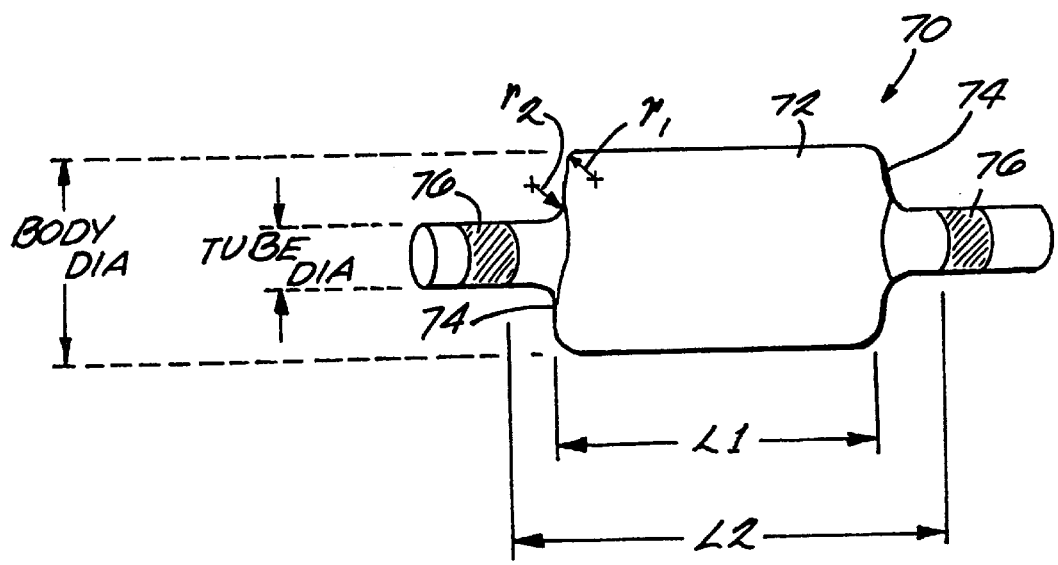
FIG. 16 is a side view of an improved expandable structure, when in a substantially expanded condition, which includes end regions having compound curvatures that reduce the end region length and thereby provide the capability of maximum bone compaction substantially along the entire length of the structure.

FIG. 16 shows an improved structure 70 having a geometry, when substantially expanded, which mitigates the tradeoff between maximum compaction diameter and effective compaction length. The structure 70 includes a middle region 72, where $BODY_{DIA}$ occurs. The structure 70 also includes end regions 74, which extend from the middle region 72 to the regions 76, where the material of the structure is bonded to the catheter tube 78, at $TUBE_{DIA}$. The catheter tube 78 can, at its proximal end, be configured like the tube 50 shown in FIG. 3, with a handle 51 made of, e.g., a foam material.

In the embodiment shown in FIG. 16, the end regions 74 are molded or stressed to provide a non-conical diameter transformation between $BODY_{DIA}$ and $TUBE_{DIA}$. The diameter changes over two predefined radial sections $r_1$, and $r_2$, forming a compound curve in the end regions 74, instead of a cone. The non-conical diameter transformation of radial sections $r_1$, and $r_2$ between $BODY_{DIA}$ and $TUBE_{DIA}$ reduces the differential between the effective bone compaction length L1 of the structure 70 and the overall length L2 of the structure 70, measured between the bond regions 76.

FIG. 17 shows another improved expandable structure 80 having a geometry mitigating the tradeoff between maximum compaction diameter and effective compaction length. Like the structure 70 shown in FIG. 16, the structure 80 in FIG. 16 includes a middle region 82 of $BODY_{DIA}$ and end regions 84 extending from the middle region to the bonded regions 86, at $TUBE_{DIA}$. As the structure 70 in FIG. 16, the end regions 84 of the structure 80 make a non-conical diameter transformation between $BODY_{DIA}$ and $TUBE_{DIA}$. In FIG. 17, the predefined radial sections $r_1$ and $r_2$ are each reduced, compared to the radial section $r_1$, and $r_2$ in FIG. 16. As a result, the end regions 84 take on an inverted profile. As a result, the entire length L2 between the bonded regions 86 becomes actually less than the effective length L1 of maximum diameter $BODY_{DIA}$. The catheter tube can, at its proximal end, be configured like the tube 50 shown in FIG. 3, with a handle 51 made of, e.g., a foam material.

The structures 70 and 80, shown in FIGS. 16 and 17, when substantially inflated, present, for a given overall length L2, regions of increasingly greater proportional length L1, where maximum cancellous bone compaction occurs.

Furthermore, as in FIG. 17, the end regions 84 are inverted about the bonded regions 86. Due to this inversion, bone compaction occurs in cancellous bone surrounding the bonded regions 86. Inversion of the end regions 84 about the bonded regions 86 therefore makes it possible to compact cancellous bone along the entire length of the expandable structure 80.

FIG. 18 shows another embodiment of an improved expandable structure 90. Like the structure 80 shown in FIG. 17, the structure 90 includes a middle region 92 and fully inverted end regions 94 overlying the bond regions 96. The structure 80 comprises, when substantially collapsed, a simple tube. At least the distal end of the tubular structure 80 is mechanically tucked or folded inward and placed into contact with the catheter tube 98. As shown in FIG. 18, both proximal and distal ends of the tubular structure are folded over and placed into contact with the catheter tube 98. The catheter tube 98 can, at its proximal end, be configured like the tube 50 shown in FIG. 3, with a handle 51 made of, e.g., a foam material.

The catheter tube 98 is dipped or sprayed beforehand with a material 102 that absorbs the selected welding energy, for example, laser energy. The folded-over ends 94 are brought into abutment against the material 102. The welding energy transmitted from an external source through the middle region 92 is absorbed by the material 102. A weld forms, joining the material 102, the folded-over ends 94, and the catheter tube 50. The weld constitutes the bond regions 96.

The inverted end regions 94 of the structure 90 achieve an abrupt termination of the structure 90 adjacent the distal end 104 of the catheter tube 98, such that the end regions 94 and the distal catheter tube end 104 are coterminous. The structure 90 possesses a region of maximum structure diameter, for maximum cancellous bone compaction, essentially along its entire length. The structure 90 presents no portion along its length where bone compaction is substantially lessened or no cancellous bone compaction occurs.

FIGS. 19 and 20 show another embodiment of an expandable structure 110. As FIG. 20 shows, the structure 110 includes a middle region 112 of maximum diameter $BODY_{DIA}$ and inverted end regions 114, which overlie the bonded regions 116.

FIG. 19 shows the structure 110 before the end regions 114 have been inverted in the manufacturing process. As FIG. 19 shows, the structure 110 comprises, when substantially collapsed, a simple tube. To facilitate formation of the inverted end regions 114 and bonded regions 116, a two-piece catheter tube is provided, comprising an outer catheter tube 118 and an inner catheter tube 120. The inner catheter tube 120 slides within the outer catheter tube 118. The catheter tube 118 can, at its proximal end, be configured like the tube 50 shown in FIG. 3, with a handle 51 made of, e.g., a foam material.

As FIG. 19 shows, during the manufacturing process, the inner catheter tube 120 is moved a first distance d1 beyond the outer catheter tube 118. In this condition, the proximal and distal ends 122 and 124 of the tubular structure 110 are bonded, without folding over or tucking in, about the inner catheter tube 118 and the outer catheter tube 120, respectively. The unfolded ends 122 and 124 of the tubular structure 110 can then be directly exposed to conventional adhesive or melt bonding processes, to form the bonded regions 116.

Once the bonded regions 116 are formed, the inner catheter tube 120 is moved (see arrow 130 in FIG. 20) to a distance d2 (shorter than d1) from the end of the outer catheter tube 118. The shortening of the inner tube 120 relative to the outer tube 120 inverts the ends 122 and 124. The inversion creates double jointed end regions 116 shown in FIG. 20, which overlie the bonded regions 116. The relative position of the outer and inner catheter tubes 118 and 120 shown in FIG. 20 is secured against further movement, e.g., by adhesive, completing the assemblage of the structure 110.

The double jointed inverted ends 114 of the structure 110 in FIG. 20, like single jointed inverted ends 94 of the structure 90 in FIG. 18, assure that no portion of the catheter tube protrudes beyond the expandable structure. Thus, there is no region along either structure 94 or 114 where cancellous bone compaction does not occur. Like the structure 90 shown in FIG. 18, the structure 110 in FIG. 20 presents a maximum diameter for maximum cancellous bone compaction essentially along its entire length.

FIG. 21 shows another embodiment of an improved expandable structure 300 well suited for deployment in an interior body region. Like the structure 110 shown in FIGS. 19 and 20, the structure 300 in FIG. 21 includes an inner catheter tube 304 secured within an outer catheter tube 302. Like the structure 110 shown in FIGS. 19 and 20, the distal end 310 of the inner catheter tube 304 in FIG. 21 extends beyond the distal end 308 of the outer catheter tube 302.

The outer diameter of the inner catheter tube 304 is likewise smaller than the inner diameter of the outer catheter tube 302. A flow passage 312 is defined by the space between the two catheter tubes 302 and 304.

The proximal end 314 of an expandable body 306 is bonded to the distal end 308 of the outer catheter tube 302. The distal end 316 of the expandable body 306 is bonded to the distal end 310 of the inner catheter tube 304. An inflation medium 318 is conveyed into the body 306 through the flow passage 312, causing expansion of the body 306.

In FIG. 21, the physical properties of the structure 300 at the proximal body end 314 differ from the physical properties of the structure 300 at the distal body end 316. The different physical properties are created by material selection. More particularly, materials selected for the inner catheter tube 304 and the expandable body 306 are more compliant (i.e., more elastic) than the materials selected for the outer catheter tube 302. In a preferred embodiment, materials selected for the expandable body 306 and the inner catheter tube 304 possess hardness properties of less than about 90 Shore A and ultimate elongation of greater than about 450%, e.g., more compliant polyurethanes. In a preferred embodiment, materials selected for the outer catheter tube 302 possess hardness properties of greater than about 45 Shore D and ultimate elongation of less than about 450%, e.g., less compliant polyurethanes or polyethylenes.

Due to the differential selection of materials, the lack of compliance of the outer catheter tube 302 at the proximal body end 314 is counterpoised during expansion of the body 306 against the compliance of the inner catheter tube 304 at the distal body end 316. The different compliance characteristics causes the body 306, during expansion, to increase in length in proportion to its increase in diameter during expansion. By virtue of the more compliant body 306 and inner catheter tube 304, the structure 300 shown in FIG. 21 is elastic enough to conform to an interior body region, like inside a bone. Nevertheless, the structure 300 is constrained from overexpansion by attachment of the proximal end 314 of the body 306 to the less elastic outer catheter tube 302.

The bond between a given expandable structure and its associated catheter tube can be strengthened by using a $CO_2$ or NdYAG laser to weld the structure and tube materials together. Factors influencing joint strength include energy wave length, energy pulse width, pulse period, head voltage, spot size, rate of rotation, working distance, angle of attack, and material selection.

The catheter tube 302 can, at its proximal end, be configured like the tube 50 shown in FIG. 3, with a handle 51 made of, e.g., a foam material.

II. Deployment in the Vasculature

FIG. 22 shows a blood vasculature region 400. The region 400 includes a first blood vessel 402, which extends along a first axis 404. The region 400 also includes a second blood vessel 406, which branches from the first blood vessel 402 along a second axis 408 offset from the first axis 404.

FIG. 22 also shows the presence of an occlusion 410 adjacent the second blood vessel 406. The occlusion 410 can comprise, e.g., plaque buildup along the interior wall of the second blood vessel 406.

FIG. 23 shows the distal end of a tool 412, which has been introduced into the vascular region 400 for the purpose of opening the occlusion 410. The tool 412 comprises a catheter tube 416, which carries at its distal end an expandable structure 420 of the type shown in FIG. 11. The catheter tube 416 can, at its proximal end, be configured like the tube 50 shown in FIG. 3, with a handle 51 made of, e.g., a foam material.

The catheter tube 416 is introduced by conventional vascular introducer and, with fluoroscopic monitoring, steered to the targeted region 400 along a guidewire 430 deployed within the first and second vessels 402 and 406. The structure 420 is expanded using a sterile fluid, like saline or a radio-contrast medium. FIG. 23 shows the structure 420 in a substantially expanded condition.

Like the expandable structure 20 shown in FIG. 11, the main axis 422 of the structure 420 shown in FIG. 23 and the axis 424 of the catheter tube 416 are not aligned. Instead, the structure axis 422 is offset at a selected acute angle A from the catheter tube axis 424. Due to the offset angle A, the structure 420, when substantially expanded (as FIG. 23 shows), is not symmetric with respect to the catheter tube axis 424.

As FIG. 23 shows, the asymmetric expansion of the structure 420 allows the physician to maintain the catheter tube 416 in axial alignment with the first blood vessel 402, while maintaining the expandable structure 420 in axial alignment with the second blood vessel 406. In this orientation, expansion of the structure 420 within the second blood vessel 406 opens the occlusion 410. The asymmetry of the structure 420 relative to the catheter tube 416 thereby permits access to branched blood vessels without complex manipulation and steering.

III. Deflection of the Structure

In all of the foregoing embodiments, a length of the associated catheter tube extends within the expandable structure. In the embodiments shown in FIGS. 4, 11A/B, 14A/B, and 15 to 18, the enclosed catheter tube comprises an extension of the main catheter tube. In the embodiments shown in FIGS. 19 to 21, the enclosed catheter tube comprises a separate catheter tube carried by the main catheter tube.

Regardless of the particular construction (see FIG. 26), the enclosed length of catheter tube 600 provides an interior lumen 602 passing within the expandable structure 604. The lumen 602 accommodates the passage of a stiffening member or stylet 606 made, e.g., from stainless steel or molded plastic material.

The presence of the stylet 606 serves to keep the structure 604 in the desired distally straightened condition during passage through an associated guide sheath 608 toward the targeted body region 610, as FIG. 26 shows. Access to the target body region 610 through the guide sheath 608 can be accomplished using a closed, minimally invasive procedure or with an open procedure.

As shown in FIG. 27, the stylet 606 can have a preformed memory, to normally bend the distal region 612 of the stylet 606. The memory is overcome to straighten the stylet 606 when confined within the guide sheath 608, as FIG. 26 shows. However, as the structure 604 and stylet 606 advance free of the guide sheath 608 and pass into the targeted region 610, the preformed memory bends the distal stylet region 612. The bend of the distal stylet region 612 bends the tube 600 and thereby shifts the axis 614 of the attached expandable structure 604 relative to the axis 616 of the access path (i.e., the guide sheath 608). The prebent stylet 606, positioned within the interior of the structure 604, further aids in altering the geometry of the structure 604 in accordance with the orientation desired when the structure 604 is deployed for use in the targeted region 610.

IV. Material Selection

In any of the foregoing embodiments, the material of the expandable structure can be selected according to the therapeutic objectives surrounding its use. For example, materials including vinyl, nylon, polyethylenes, ionomer, polyurethane, and polyethylene tetraphthalate (PET) can be used. The thickness of the structure is typically in the range of 2/1000ths to 25/1000ths of an inch, or other thicknesses that can withstand pressures of up to, for example, 250–500 psi.

If desired, the material for the structure can be selected to exhibit generally elastic properties, like latex. Alternatively, the material can be selected to exhibit less elastic properties, like silicone. Using expandable bodies with generally elastic or generally semi-elastic properties, the physician monitors the expansion to assure that over-expansion and wall failure do not occur. Furthermore, expandable bodies with generally elastic or generally semi-elastic properties may require some form of external or internal restraints to assure proper deployment in bone. The use of internal or external restraints in association with expandable bodies used to treat bone is discussed in greater detail in copending U.S. patent application Ser. No. 08/485,394, filed Jun. 7, 1995, which is incorporated herein by reference.

Generally speaking, for use in treating bone, providing relatively inelastic properties for the expandable structure, while not always required, is nevertheless preferred, when maintaining a desired shape and size within the bone is important, for example, in a vertebral body, where the spinal cord is nearby. Using relatively inelastic bodies, the shape and size can be better predefined, taking into account the normal dimensions of the outside edge of the cancellous bone. Use of relatively inelastic materials also more readily permits the application of pressures equally in a defined geometry to compress cancellous bone.

When treating bone, the choice of the shape and size of a expandable structure takes into account the morphology and geometry of the site to be treated. The shape of the cancellous bone to be compressed, and the local structures that could be harmed if bone were moved inappropriately, are generally understood by medical professionals using textbooks of human skeletal anatomy along with their knowledge of the site and its disease or injury. The physician is also able to select the materials and geometry desired for the structure based upon prior analysis of the morphology of the targeted bone using, for example, plain films, spinous process percussion, or MRI or CRT scanning. The materials and geometry of the structure are selected to optimize the formation of a cavity that, when filled with bone cement, provide support across the middle region of the bone being treated.

In some instances, it is desirable, when creating a cavity, to also move or displace the cortical bone to achieve the desired therapeutic result. Such movement is not per se harmful, as that term is used in this Specification, because it is indicated to achieve the desired therapeutic result. By definition, harm results when expansion of the structure results in a worsening of the overall condition of the bone and surrounding anatomic structures, for example, by injury to surrounding tissue or causing a permanent adverse change in bone biomechanics.

As one general guideline, the selection of the geometry of the expandable structure should take into account that at least 40% of the cancellous bone volume needs to be compacted in cases where the bone disease causing fracture (or the risk of fracture) is the loss of cancellous bone mass (as in osteoporosis). The preferred range is about 30% to 90% of the cancellous bone volume. Compacting less of the cancellous bone volume can leave too much of the diseased cancellous bone at the treated site. The diseased cancellous bone remains weak and can later collapse, causing fracture, despite treatment.

Another general guideline for the selection of the geometry of the expandable structure is the amount that the targeted fractured bone region has been displaced or depressed. The expansion of the structure within the cancellous bone region inside a bone can elevate or push the fractured cortical wall back to or near its anatomic position occupied before fracture occurred.

However, there are times when a lesser amount of cancellous bone compaction is indicated. For example, when the bone disease being treated is localized, such as in avascular necrosis, or where local loss of blood supply is killing bone in a limited area, the expandable structure can compact a smaller volume of total bone. This is because the diseased area requiring treatment is smaller.

Another exception lies in the use of an expandable structure to improve insertion of solid materials in defined shapes, like hydroxyapatite and components in total joint replacement. In these cases, the structure shape and size is defined by the shape and size of the material being inserted.

Yet another exception lays the use of expandable bodies in bones to create cavities to aid in the delivery of therapeutic substances, as disclosed in copending U.S. patent application Ser. No. 08/485,394, previously mentioned. In this case, the cancellous bone may or may not be diseased or adversely affected. Healthy cancellous bone can be sacrificed by significant compaction to improve the delivery of a drug or growth factor which has an important therapeutic purpose. In this application, the size of the expandable structure is chosen by the desired amount of therapeutic substance sought to be delivered. In this case, the bone with the drug inside is supported while the drug works, and the bone heals through exterior casting or current interior or exterior fixation devices.

The materials for the catheter tube are selected to facilitate advancement of the expandable structure into cancellous bone. The catheter tube can be constructed, for example, using standard flexible, medical grade plastic materials, like vinyl, nylon, polyethylenes, ionomer, polyurethane, and polyethylene tetraphthalate (PET). The catheter tube can also include more rigid materials to impart greater stiffness and thereby aid in its manipulation. More rigid materials that can be used for this purpose include stainless steel, nickel-titanium alloys (Nitinol™ material), and other metal alloys.

V. Single Use

Expansion of any one of the expandable structures described herein during first use in a targeted body region generates stress on the material or materials which make up the structure. The material stress created by operational loads during first use in a targeted body region can significantly alter the molded morphology of the structure, making future performance of the structure unpredictable.

For example, expansion within bone during a single use creates contact with surrounding cortical and cancellous bone. This contact can damage the structure, creating localized regions of weakness, which may escape detection. The existence of localized regions of weakness can unpredictably cause overall structural failure during a subsequent use.

In addition, exposure to blood and tissue during a single use can entrap biological components on or within the structure or the associated catheter tube. Despite cleaning and subsequent sterilization, the presence of entrapped biological components can lead to unacceptable pyrogenic reactions.

As a result, following first use, the structure can not be relied upon to reach its desired configuration during subsequent use and may not otherwise meet established performance and sterilization specifications. The effects of material stress and damage caused during a single use, coupled with the possibility of pyrogen reactions even after resterilization, reasonably justify imposing a single use restriction upon devices which carry these expandable structures for deployment in bone.

Figure 24:
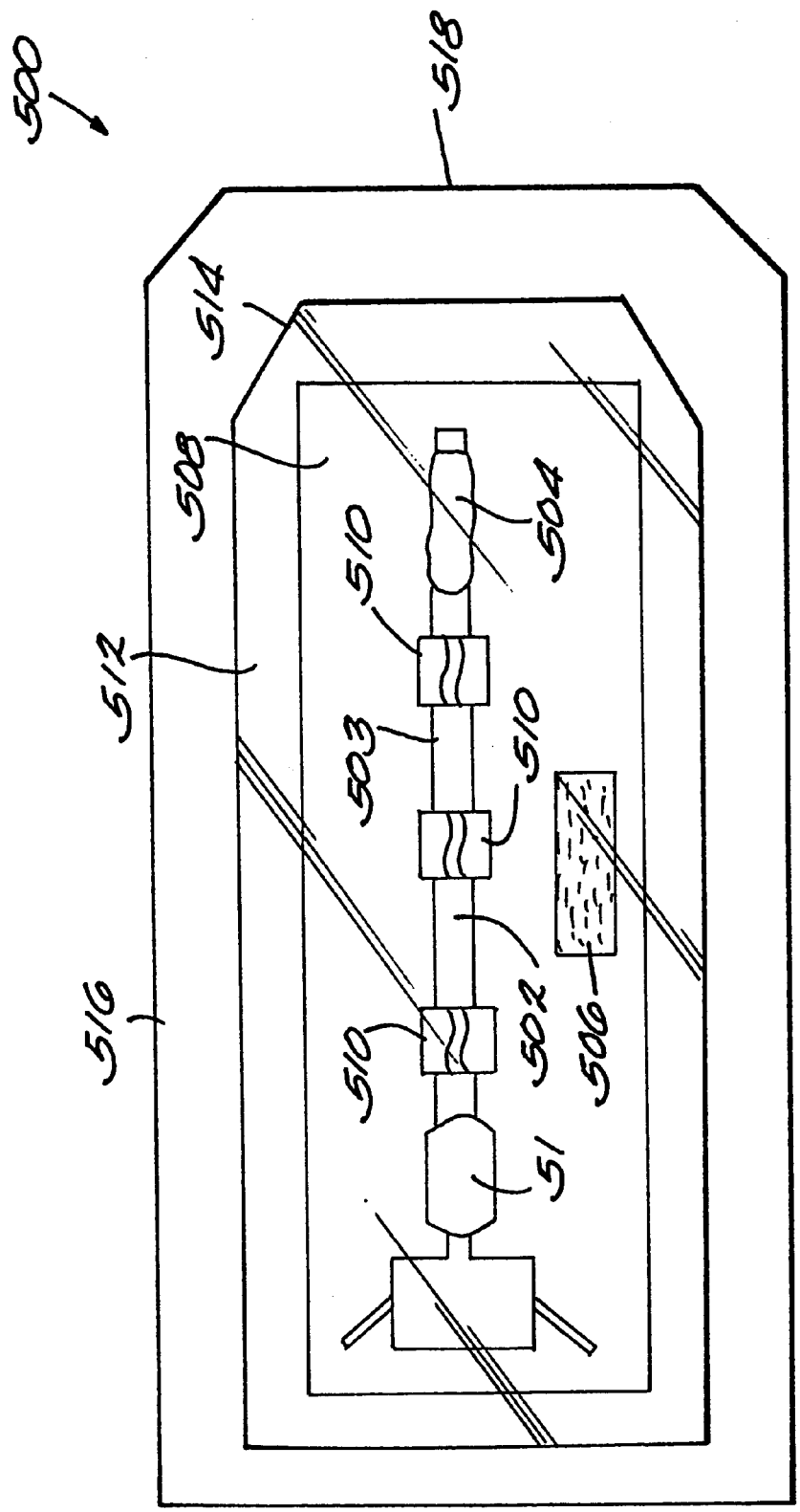
FIG. 24 is a plan view of a sterile kit to store a single use probe, which carries an expandable structures as previously shown.
Figure 25:
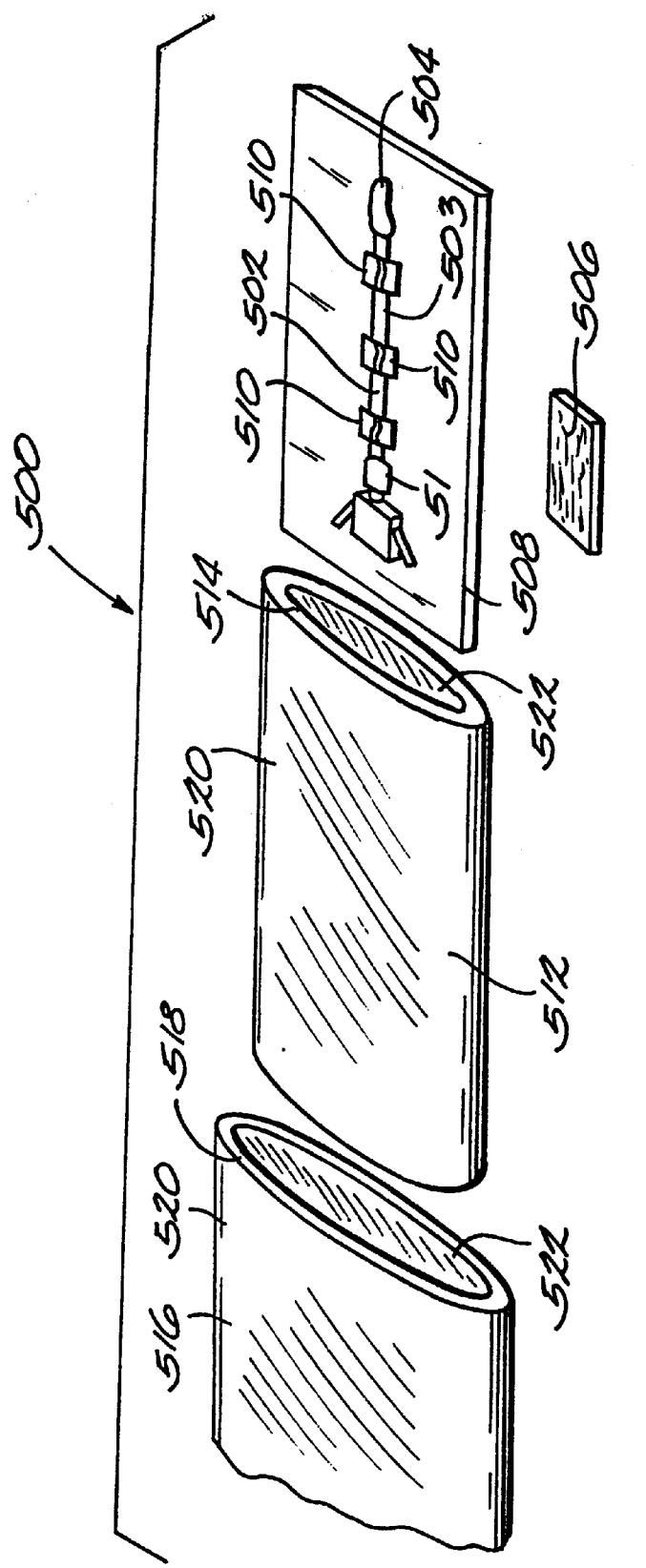
FIG. 25 is an exploded perspective view of the sterile kit shown in FIG. 24.

To protect patients from the potential adverse consequences occasioned by multiple use, which include disease transmission, or material stress and instability, or decreased or unpredictable performance, the invention also provides a kit 500 (see FIGS. 24 and 25) for storing a single use probe 502, which carries an expandable structure 504 described herein prior to deployment in bone.

In the illustrated embodiment (see FIGS. 24 and 25), the kit 500 includes an interior tray 508. The tray 508 holds the probe 502 in a lay-flat, straightened condition during sterilization and storage prior to its first use. The tray 508 can be formed from die cut cardboard or thermoformed plastic material. The tray 508 includes one or more spaced apart tabs 510, which hold the catheter tube 503 and expandable structure 504 in the desired lay-flat, straightened condition. As shown, the facing ends of the tabs 510 present a nesting, serpentine geometry, which engages the catheter tube 503 essentially across its entire width, to securely retain the catheter tube 503 on the tray 508.

The kit 500 includes an inner wrap 512, which is peripherally sealed by heat or the like, to enclose the tray 508 from contact with the outside environment. One end of the inner wrap 512 includes a conventional peal-away seal 514 (see FIG. 25), to provide quick access to the tray 508 upon instance of use, which preferably occurs in a sterile environment, such as within an operating room.

The kit 500 also includes an outer wrap 516, which is also peripherally sealed by heat or the like, to enclosed the inner wrap 512. One end of the outer wrap 516 includes a conventional peal-away seal 518 (see FIG. 25), to provide access to the inner wrap 512, which can be removed from the outer wrap 516 in anticipation of imminent use of the probe 502, without compromising sterility of the probe 502 itself.

Both inner and outer wraps 512 and 516 (see FIG. 25) each includes a peripherally sealed top sheet 520 and bottom sheet 522. In the illustrated embodiment, the top sheet 520 is made of transparent plastic film, like polyethylene or MYLAR™ material, to allow visual identification of the contents of the kit 500. The bottom sheet 522 is made from a material that is permeable to EtO sterilization gas, e.g., TYVEC™ plastic material (available from DuPont).

The sterile kit 500 also carries a label or insert 506, which includes the statement "For Single Patient Use Only" (or comparable language) to affirmatively caution against reuse of the contents of the kit 500. The label 506 also preferably affirmatively instructs against resterilization of the probe 502. The label 506 also preferably instructs the physician or user to dispose of the probe 502 and the entire contents of the kit 500 upon use in accordance with applicable biological waste procedures. The presence of the probe 502 packaged in the kit 500 verifies to the physician or user that probe 502 is sterile and has not be subjected to prior use. The physician or user is thereby assured that the expandable structure 504 meets established performance and sterility specifications, and will have the desired configuration when expanded for use.

The features of the invention are set forth in the following claims.

We claim:

1. A method for treating bone comprising the steps of providing a tool comprising an outer catheter tube having a distal end, an inner catheter tube extending within the outer catheter tube and having a distal end region that extends beyond the distal end of the outer catheter tube, and an expandable structure having a proximal end secured to the distal end of the outer catheter tube and a distal end secured to the distal end region of the inner catheter tube, whereby the distal end region of the inner catheter tube is enclosed within the expandable structure, manipulating the tool to introduce the expandable structure into bone while in a generally collapsed geometry, and causing the expandable structure to assume an expanded geometry inside bone.

2. A method according to claim 1 wherein, when assuming the expandable geometry, the expandable structure compacts cancellous bone.

3. A method according to claim 1 wherein, when assuming the expandable geometry, the expandable structure compacts cancellous bone and forms a cavity.

4. A method according to claim 1 further including the step of convey material into the cavity.

5. A method according to claim 4 wherein the material comprises bone cement.

6. A method according to claim 1 wherein, when assuming the expandable geometry the expandable structure exerts interior force upon cortical bone.

7. A method according to claim 1 wherein, when assuming the expandable geometry, the expandable structure exerts interior force upon cortical bone to move fractured cortical bone.

8. A method according to claim 1 wherein the proximal and distal ends of the expandable structure are inverted about the distal end of the outer catheter tube and distal end region of the inner catheter tube, respectively.

9. A method according to claim 1 wherein the inner catheter tube is more compliant than the outer catheter tube.

10. A method according to claim 1 wherein the inner catheter tube and expandable structure are more compliant than the outer catheter tube.

* * * * *